United States Patent
Dreyfuss et al.

(10) Patent No.: US 10,898,179 B2
(45) Date of Patent: *Jan. 26, 2021

(54) SYSTEMS FOR LOCKING A CINCH LOOP IN TISSUE REPAIR

(71) Applicant: Arthrex, Inc., Naples, FL (US)

(72) Inventors: Peter J. Dreyfuss, Naples, FL (US); Derek C. Sullivan, Bonita Springs, FL (US)

(73) Assignee: Arthrex, Inc., Naples, FL (US)

( * ) Notice: Subject to any disclaimer, the term of this patent is extended or adjusted under 35 U.S.C. 154(b) by 132 days.

This patent is subject to a terminal disclaimer.

(21) Appl. No.: 16/282,912

(22) Filed: Feb. 22, 2019

(65) Prior Publication Data

US 2019/0192133 A1 Jun. 27, 2019

Related U.S. Application Data

(63) Continuation of application No. 14/043,277, filed on Oct. 1, 2013, now Pat. No. 10,258,320.

(Continued)

(51) Int. Cl.
*A61B 17/04* (2006.01)
*A61B 17/06* (2006.01)
*A61F 2/08* (2006.01)

(52) U.S. Cl.
CPC ...... *A61B 17/0401* (2013.01); *A61B 17/0487* (2013.01); *A61B 17/06166* (2013.01); *A61F 2/0811* (2013.01); *A61B 17/0485* (2013.01); *A61B 2017/0412* (2013.01); *A61B 2017/0414* (2013.01); *A61B 2017/0458* (2013.01); *A61B 2017/06176* (2013.01); *A61B 2017/06185* (2013.01); *A61F 2002/0852* (2013.01); *A61F 2002/0882* (2013.01)

(58) Field of Classification Search
CPC .............. A61F 17/0401; A61F 17/0485; A61F 17/0487; A61F 17/06166; A61F 2017/0412; A61F 2017/0414; A61F 2017/06176; A61F 2002/0852; A61F 2002/0882

See application file for complete search history.

(56) References Cited

U.S. PATENT DOCUMENTS 3,716,058 A 2/1973 Tanner, Jr.
6,296,659 B1 * 10/2001 Foerster ............. A61B 17/0469
606/224

(Continued)

FOREIGN PATENT DOCUMENTS

EP  2 108 316 A1  10/2009
EP  2 572 648 A1  3/2013
EP  2 581 047 A1  4/2013

*Primary Examiner* — Majid Jamialahmadi
(74) *Attorney, Agent, or Firm* — Blank Rome LLP

(57) ABSTRACT

Systems and methods for soft tissue to bone repairs, without knot tying. The soft tissue repair systems include self-cinching constructs with splices, loops and inserts that are pre-loaded onto knotless anchors to position the self-locking, adjustable construct at the repair site. The splice incorporates an insert in the form of a flexible strand with at least one barb, or simply in the form of a cut length of suture or braid that is inserted into the center of the cinching loop to create a thicker portion. When the cinching loop is tightened, the insert prevents loosening of the loop, locking in the cinching loop and preventing movement of the loop.

11 Claims, 20 Drawing Sheets

Related U.S. Application Data

(60) Provisional application No. 61/719,018, filed on Oct. 26, 2012.

(56) References Cited

U.S. PATENT DOCUMENTS

| | | |
|---|---|---|
| 7,601,165 B2 | 10/2009 | Stone |
| 2003/0050666 A1 | 3/2003 | Grafton |
| 2004/0093031 A1 | 5/2004 | Burkhart et al. |
| 2008/0004659 A1 | 1/2008 | Burkhart et al. |
| 2008/0051835 A1 | 2/2008 | Mazzocca |
| 2008/0140092 A1 | 6/2008 | Stone et al. |
| 2008/0255613 A1* | 10/2008 | Kaiser ............... A61B 17/06166 606/232 |
| 2010/0256677 A1 | 10/2010 | Albertorio et al. |
| 2010/0268273 A1 | 10/2010 | Albertorio et al. |
| 2012/0053630 A1 | 3/2012 | Denham et al. |
| 2012/0143349 A1* | 6/2012 | Peterson .......... A61B 17/06166 623/23.72 |
| 2012/0277770 A1 | 11/2012 | Fenton |
| 2013/0096611 A1 | 4/2013 | Sullivan |

* cited by examiner

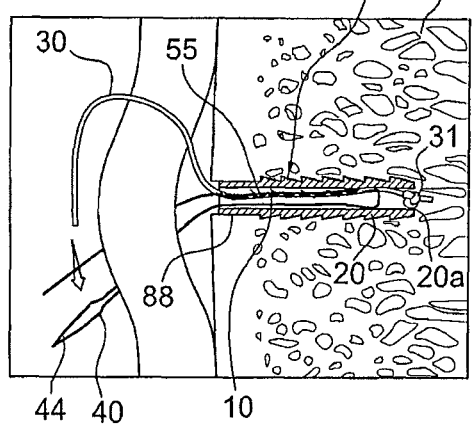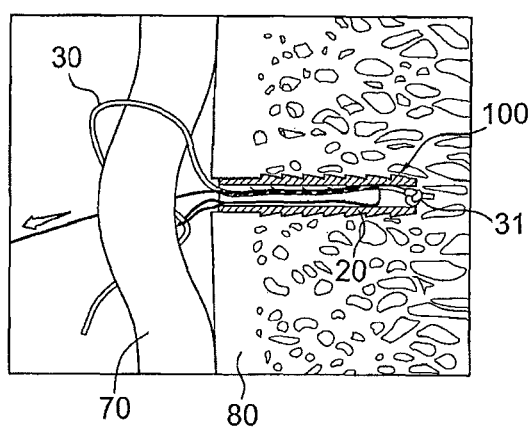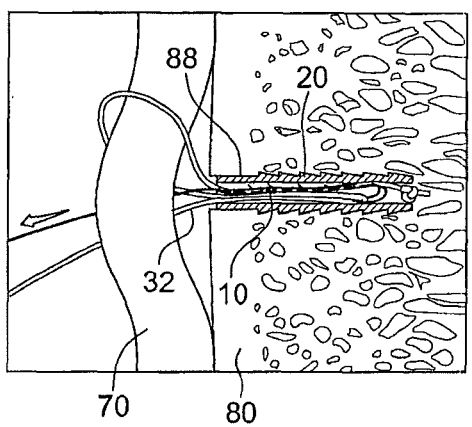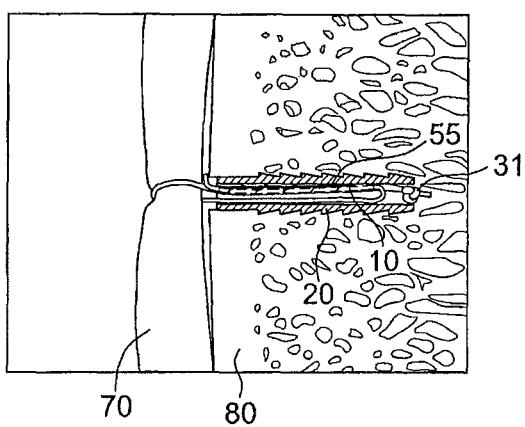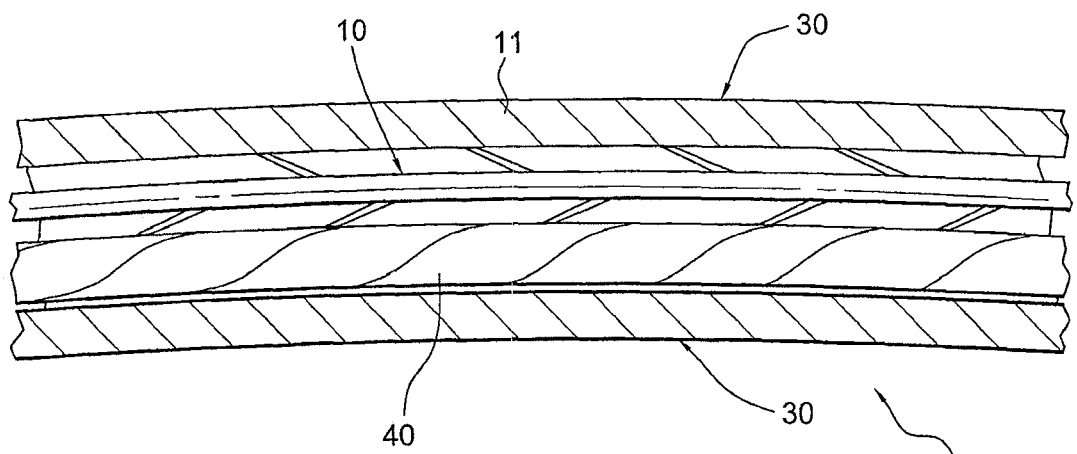

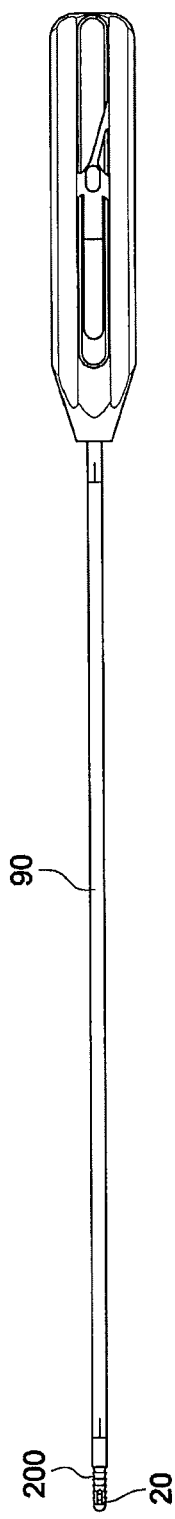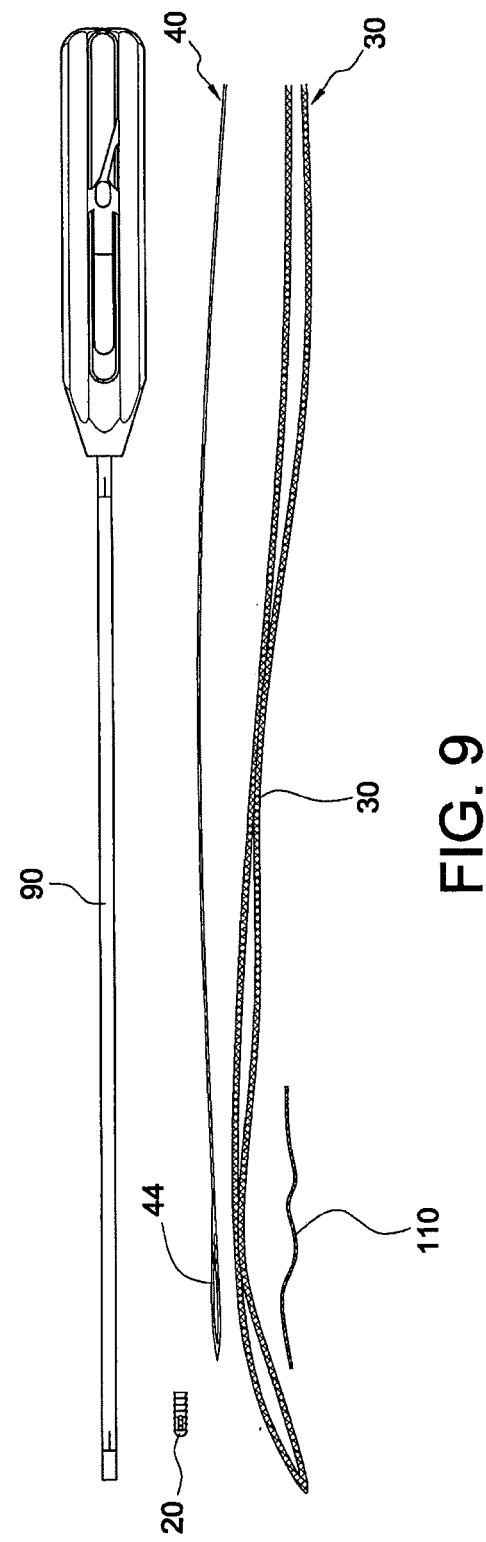

SYSTEMS FOR LOCKING A CINCH LOOP IN TISSUE REPAIR

CROSS-REFERENCE TO RELATED APPLICATIONS

This application is a continuation of application Ser. No. 14/043,277, filed Oct. 1, 2013, which claims the benefit of U.S. Provisional Application No. 61/719,018 filed Oct. 26, 2012, the disclosures of which are incorporated by reference in their entireties herein.

FIELD OF THE INVENTION

The present invention relates to surgical devices and, in particular, to devices for repair or fixation of soft tissue to bone without the need for knots.

BACKGROUND OF THE INVENTION

Knotless suture devices and repairs and known in the art. For example, a knotless suture anchor is disclosed in U.S. Pat. No. 7,329,272 (a two piece Arthrex PushLock® anchor) to facilitate tissue fixation to bone. Similarly, a knotless anchor that allows tensioning of the suture as necessary and after insertion into bone is disclosed in U.S. Pat. No. 9,107,653, the disclosure of which is incorporated by reference in its entirety herewith.

As detailed in U.S. Pat. No. 9,107,653, the knotless suture anchor has a configuration which allows the suture to be spliced and passed through itself within the suture anchor, to create a construct (knotless adjustable cinching loop) that is tensionable after insertion in bone (to allow attached tissue to be brought proximate to bone) and without requiring tying of any knots. The suture is spliced by providing a shuttle/pull device (in the form of a suture passing device such as a FiberLink™ or a nitinol loop) attached to a flexible strand and within the body of a suture anchor, and by pulling on the shuttle/pull device subsequent to the suture anchor being secured into the bone. In this manner, the final construct includes a knotless self-locking mechanism (knotless adjustable cinching loop) that allows the user (the surgeon) to control the tension of the suture strand on the soft tissue to be attached to bone, and to also control the location of the tissue with respect to the bone.

There is a need for a knotless anchor construct which has a knotless adjustable cinching loop that is secured and locked at the end of the tensioning of the construct. Also needed are methods of locking a cinching loop to prevent loosening of the loop and pulling out of the fixation device (anchor). Also needed is a tensionable anchor that does not require tying of knots and allows improved adjustment of both the tension of the suture and the location of the tissue with respect to the bone.

SUMMARY OF THE INVENTION

The present invention fulfills the above needs and objectives by providing knotless, tensionable suture anchors and methods of tissue repairs with such anchors. The suture anchor of the present invention has a configuration which allows the suture to be spliced and passed through itself, to create a construct with a splice and a cinching loop that is tensionable after insertion in bone (to allow attached tissue to be brought proximate to bone) and does not require tying of any knots. The splice incorporates an insert (locking mechanism) in the form of a flexible strand with at least one barb, or simply in the form of a cut length of suture that is inserted into the center of the cinching loop to create a thicker portion. When the cinching loop is tightened, the insert (locking mechanism) prevents loosening of the loop, locking in the cinching loop and preventing movement of the loop.

Other features and advantages of the present invention will become apparent from the following description of the invention.

BRIEF DESCRIPTION OF THE DRAWINGS

FIGS. 4-7 illustrate subsequent steps of a method of knotless soft tissue fixation (SutureTak™ self-locking technology) according to an exemplary method of the present invention and with the flexible strand with barbs of FIG. 3.

FIG. 8 is a schematic cross-sectional view of the splice of the surgical construct of FIG. 7.

FIGS. 9-55 illustrate subsequent steps of a method of assembling a surgical construct of the present invention (with an insert in the form of an exemplary cut length of suture).

DETAILED DESCRIPTION OF THE EMBODIMENTS

Figure 1:
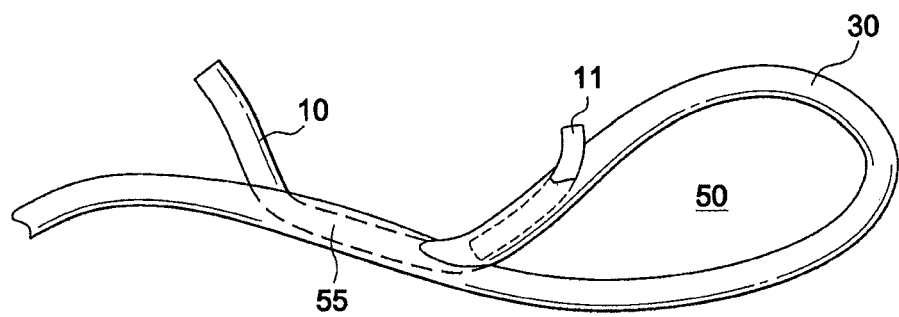
FIG. 1 illustrates a cinching loop with barbs according to an exemplary embodiment of the present invention (in the unlocked position).

The present invention provides surgical constructs, systems and techniques for knotless soft tissue repairs and fixations, such as fixation of soft tissue (ligament, tendon, graft, etc.) to bone.

In an exemplary embodiment, the surgical construct is a soft anchor (an all-suture anchor) that is a tensionable knotless construct consisting of a cinching loop (formed of a flexible strand such as suture) with a suture insert (locking mechanism) attached to the cinching loop through a splice in the flexible strand. The suture insert is a barbed insert in the form of another flexible strand provided with a plurality of barbs (spikes or similar structures). The cinching loop is tensionable (to allow attached tissue to be brought proximate to bone, for example) and does not require tying of any knots. The splice incorporates the suture insert (the flexible strand with at least one barb). When the cinching loop is tightened, the barbs prevent loosening of the loop by digging in when a loosening force is applied and locking in the cinching loop (preventing movement of the loop). The knotless, adjustable soft anchor (all-suture anchor) is formed essentially of suture (or similar material) and does not incorporate an anchor body.

In another exemplary embodiment, the surgical construct is also a soft anchor (an all-suture anchor formed only of suture) that is a tensionable knotless construct consisting of a cinching loop (formed of a flexible strand such as suture) but with an insert (locking mechanism) in the form of a cut length of suture. The cut length of suture is inserted into the center of a coreless suture to create a thicker portion. This thicker portion is at a set length so that, when the repair is completed, the thicker portion ends up inside the splice of the final construct.

In yet other exemplary embodiments, the surgical constructs of the present invention comprise fixation devices (tensionable knotless anchors) that are inserted into bone with a flexible strand (a suture) provided within the fixation device and a shuttle/pull device (a suture passing instrument) attached to the flexible strand. An insert (locking mechanism) is also provided with the shuttle/pull device (suture passing instrument) to prevent movement of the suture during and after the formation of the splice and cinching loop. The insert may be a barbed insert in the form of a flexible strand with a plurality of barbs (spikes or similar structures), or simply a cut length of suture that is inserted into the center of a coreless suture to create a thicker portion. The flexible strand, the shuttle/pull device attached to it, and the insert allow the formation of a splice within the body of the anchor and during the tissue repair procedure (to finalize the construct).

The shuttle/pull device and the insert (length of suture or strand with barbs) are provided within the flexible strand (inside of the flexible strand) and form the splice and a cinching loop subsequent to the insertion of the fixation device within the bone (and subsequent to attachment to soft tissue to be repaired or fixated) to allow formation of the final fixation device with a knotless self-locking mechanism that allows the user (for example, the surgeon) to control the tension of the strand on the soft tissue to be attached to bone.

If the insert is formed of a strand with barbs, the barbs are oriented so to prevent loosening of the cinching loop (and of the final construct) when a loosening force is applied. The suture insert (strand with barbs) will resist traveling/moving in opposite direction due to the barbs/spikes. The barbs confer additional locking (reinforced locking) to the final construct (the primary locking being provided by the splice itself).

If the insert is formed of a length of flexible strand (for example, suture such as a 2-0 FiberWire® suture), then the suture is inserted into the center of a coreless suture to create a thicker portion. This thicker portion is at a set length so that, when the repair is completed, the thicker portion ends up inside the splice of the final construct. Advantages of this design include the following: (i) as the thicker portion enters the sheath of the splice, it takes up more space and creates more surface area contact between the outer jacket of the splice and itself, increasing the pullout strength; and (ii) when the tension is set, the outer jacket grabs onto the thicker inner suture sooner; this aspect helps resist loosening from probing.

The present invention also provides methods of soft tissue repair which do not require tying of knots and allow adjustment of both the tension of the suture and the location of the tissue with respect to the bone. An exemplary method of the present invention comprises inter alia the steps of: (i) providing a soft anchor (an all-suture anchor) consisting of a flexible strand forming a cinching, knotless loop with a suture insert (a cut flexible strand, or a suture with barbs or spikes) attached to the cinching loop through a splice of the cinching loop, and attaching soft tissue to be fixated (or reattached) to the soft anchor; and (ii) pulling on the flexible strand to allow the soft tissue to achieve the desired location relative to bone, to allow proper tensioning of the final construct, and to lock the cinching loop and prevent movement of the loop by the thickness of the cut strand or by the orientation of the barbs (spikes).

Another exemplary method of the present invention comprises inter alia the steps of: (i) providing a surgical construct comprising a fixation device (for example, an anchor) with a flexible strand (for example, suture) extending through the body of the fixation device and with a shuttle/pull device (a suture passing instrument) attached to the flexible strand and further with an insert (for example, a cut-to-length suture, or a suture with barbs or spikes) attached to the flexible strand; (ii) inserting the fixation device into bone; (iii) passing the flexible strand around or through tissue to be fixated (or reattached) to bone, and then through an eyelet/loop of the shuttle/pull device; (iv) subsequently, pulling on the shuttle/pull device to allow the flexible strand to double on itself and to form a cinching loop and a splice within the body of the fixation device (with the flexible strand passing through itself) and with the suture strand or suture with barbs located within the body of the splice; and (v) pulling on the flexible strand to allow the soft tissue to achieve the desired location relative to the bone, to allow proper tensioning of the final construct, and to lock the cinching loop and prevent movement of the loop by the insert (thickness of the suture strand or barbs (spikes) of the suture).

Figure 2:
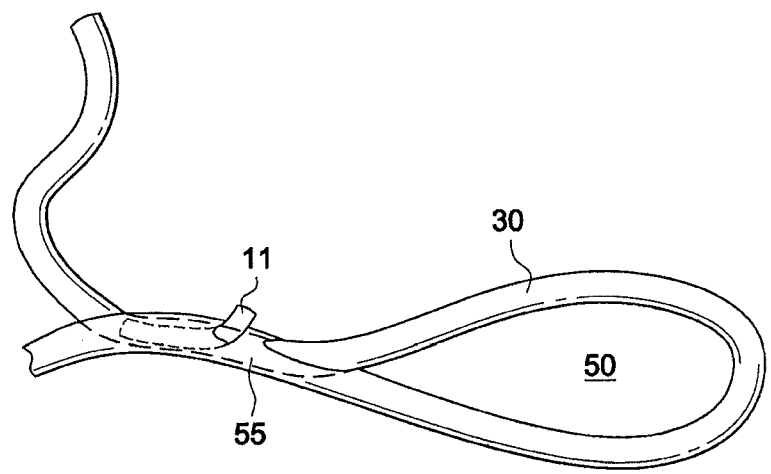
FIG. 2 illustrates the cinching loop with barbs of FIG. 1 in the locked position.
Figure 3:
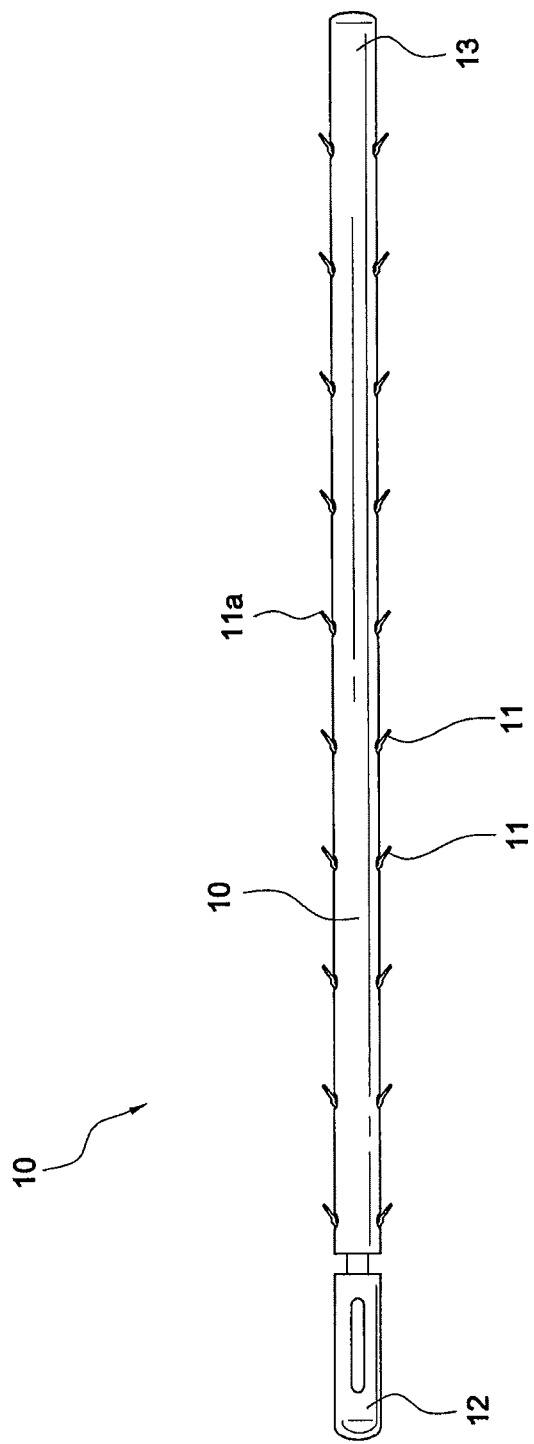
FIG. 3 illustrates an exemplary embodiment of a barbed insert (a flexible strand (suture) with barbs or spikes).

Referring now to the drawings, where like elements are designated by like reference numerals, FIGS. 1-3 illustrate an exemplary cinching loop 50 with a suture insert 10 of the present invention which may be employed by itself and/or to assemble surgical construct 100 (FIG. 4). In the particular exemplary embodiment illustrated in FIGS. 1-3, suture insert 10 is a flexible strand of material such as suture provided with at least one barb or spike 11, preferably with a plurality of barbs or spikes 11 (shown more clearly in FIG. 3). Barbs or spikes 11 may have any geometry and/or configuration that allow insertion/fixation of these structures within a flexible strand (such as a suture strand) but then prevent movement while inserted/fixed within such material. For example, barbs or spikes 11 may have an elongated conical configuration with a very sharp point or tip 11a (FIG. 3) to permit easy penetration along a length of a suture strand (when the insert 10 is pulled in a first direction) but to prevent movement in the opposite direction (i.e., when the insert is pulled in a second direction which is different from the first direction, for example, opposite the first direction). Barbs or spikes 11 extend substantially along the length of suture insert 10 (except the proximal end 12 and distal end 13). Barbs or spikes 11 may also extend substantially around the length of suture insert 10 (except the proximal end 12 and distal end 13) and they have about the same orientation (direction) relative to the longitudinal axis of the suture insert 10. Barbs or spikes 11 may be integral to the suture insert 10 (i.e., manufactured with the suture insert by insert molding, for example) or may be attached to the suture insert by any known methods in the art.

In an exemplary-only embodiment, the cinching loop 50 of FIGS. 1 and 2 may form a soft anchor (an all-suture anchor) that consists of cinching loop 50 and insert 10 attached to the loop 50 through splice 55. Cinching loop 50 is formed of a flexible strand 30 (a suture strand 30). Suture insert 10 is attached to the flexible strand through splice 55. In this embodiment, the knotless, adjustable anchor construct (surgical construct) is formed essentially of suture (i.e., without an anchor body) and the locking of the construct (around tissue to be fixated or secured to bone) is provided by the barbs (spikes) that prevent movement of the flexible strand.

According to another exemplary embodiment, and as detailed below, the cinching loop 50 of FIGS. 1 and 2 includes flexible strand 30 (suture strand 30), insert 10 attached to the flexible strand through splice 55, and also a shuttle/pull device 40 (for example, a suture passing device 40 such as FiberLink™ 40 or a nitinol loop 40) attached to the flexible strand 30 also through the splice 55.

FIGS. 4-7 illustrate surgical system 100 including a knotless tensionable anchor 20, with suture 30 (having suture passing device 40 and suture insert 10 attached to the suture 30 through splice 55 of loop 50) employed in an exemplary method of tissue repair such as a Bankart or SLAP repair, wherein the knotless suture anchor (knotless SutureTak™) simplifies arthroscopic glenohumeral joint instability repair by combining a proven and reproducible suture anchor insertion procedure with knotless soft tissue fixation.

FIG. 4 shows suture 30, preferably a UHMWPE suture, preloaded onto the anchor 20 by tying static knot 31, which prevents suture 30 from passing through distal blind hole 20*a*. Suture 30 is pre-attached to suture passing device 40 (for example, a FiberLink™ or a Nitinol loop 40) which is threaded through suture 30 (as shown by spliced region 55 in FIG. 4). Suture insert 10 is also added alongside the suture passing device (Nitinol loop 40) and inside of the splice 55. Suture 30 is pre-loaded on anchor 20 which is loaded onto a driver (not shown in FIGS. 4-7). Suture 30 is tied to the driver (for example, wrapped around a cleft of the driver) to fasten tensionable knotless anchor 20 securely to the driver. The suture passing device 40 and insert 10 (with barbs 11) are also attached (threaded through splice 55) to the suture 30. The construct is inserted into bone, the suture 30 untied from the driver, and the driver removed.

Figure 5B:
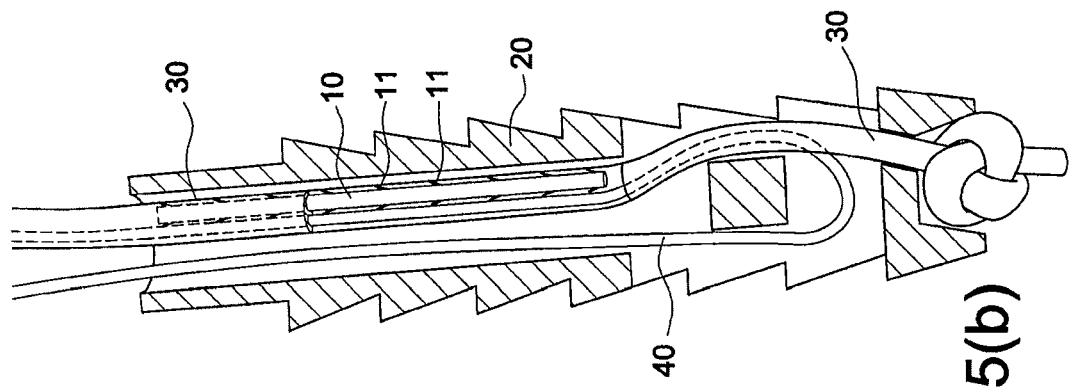
Figure 5A:
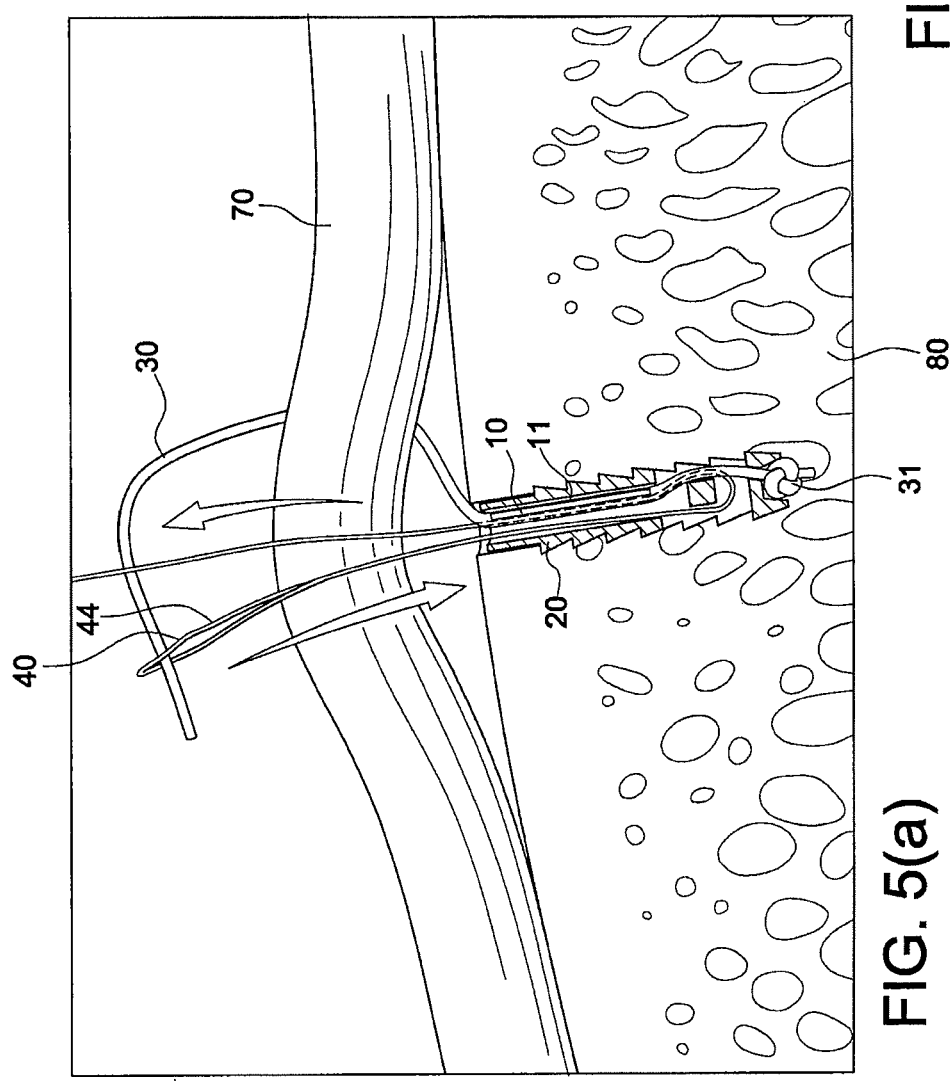

FIG. 4 depicts the tensionable knotless anchor 20 after it has been inserted into a drilled hole 88 in bone 80, the suture 30 released from the driver, and the driver removed. Suture 30 is passed through or around the tissue 70 which is to be reattached to bone 80. FIG. 5 depicts suture 30 passed around the tissue 70 and then threaded through eyelet/closed loop 44 of the suture passing device 40. FIGS. 5(*a*) and 5(*b*) are enlarged views of the embodiment shown in FIG. 5, illustrating in more detail the insertion of barbed insert 10 with barbs 11 (shown clearly in FIG. 5(*b*)) into the suture 30. Suture passing device 40 is pulled (as shown in FIG. 6), thereby pulling suture 30 and insert 10 with barbs (spikes) 11 towards tensionable knotless anchor 20. As seen in FIGS. 3 and 5(*b*), the insert 10 and the suture passing device 40 are preferably separate components from the suture 30.

In FIG. 6, suture 30 has been further pulled towards tensionable knotless anchor 20 so that it doubles on itself inside tensionable knotless anchor 20. The suture passing device 40 has also been further pulled through suture 30. FIG. 7 illustrates surgical construct 100 with suture 30 after it has been pulled through itself, creating splice 55. The suture passing device 40 (not visible anymore in FIG. 7 as it has been completely pulled out of the suture 30) helps create splice 55 within tensionable knotless anchor 20 by facilitating suture 30 passing through itself. Splice 55 contains suture insert 10 with barbs 11 that prevent movement of the suture 30 and aid in locking the final construct.

Once the suture 30 has been fully passed through itself, the suture end 32 (FIG. 6) may be pulled until tissue 70 has been moved to the desired location, such as near drilled hole 88 in the bone 80. Once the desired tension and location is achieved, suture end 32 may be clipped off to complete the soft tissue repair or fixation. In this manner, the suture 30 is shuttled and pulled (during the surgery) to a desired tension.

Barbs or spikes 11 prevent movement of the suture 30 and provide additional locking of the final construct at the desired location (the primary locking being conferred by the splice itself).

Figure 54:
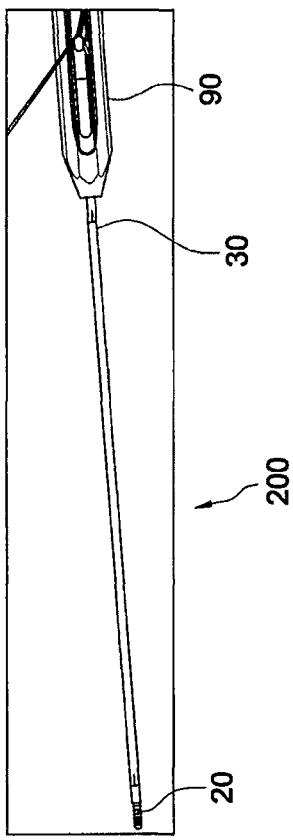
Figure 55:
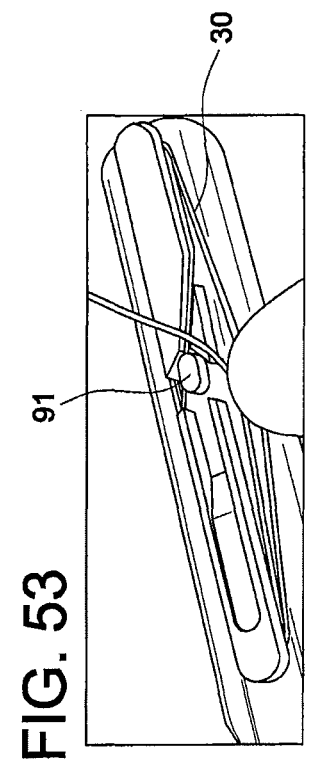

Reference is now made to FIGS. 9-55, which illustrate subsequent steps of a method of assembling another exemplary surgical construct of the present invention, i.e., surgical construct 200 of FIG. 55 (comprising a tensionable knotless anchor (knotless SutureTak™) loaded with an insert in the form of a small cut-to-length piece of suture and a suture passing device attached to the suture). Assembly instructions are provided below:

FIG. 9: illustrates exemplary materials for the surgical construct 200: driver 90, suture anchor 20; nitinol wire 40 with closed loop 44; UHMWPE braid 30; and insert 110. The suture component 30 is constructed from exemplary braided UHMWPE. Insert 110 is in the form of an exemplary 2-0 FiberWire® suture.

FIG. 10: illustrates driver 90 assembled with suture anchor 20 of the present invention.

Figure 11:
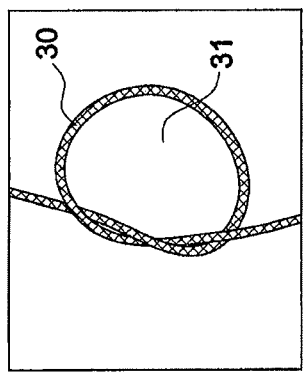

FIG. 11: Tie an overhand knot 31 within about 3 inches from one end of the braid 30. In further steps, the sides of the knot 31 will be referred to as the short end and the long end resembling the length of suture 30 on that side of the knot. Preferably, there should be no tipped suture within the vicinity of the knot.

Figure 12:
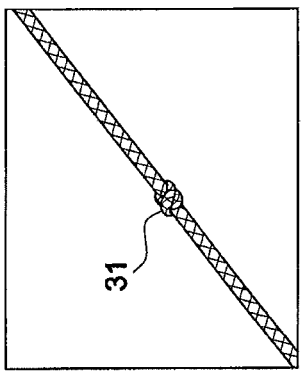

FIG. 12: Pull knot 31 tight so that knot will fit in hole of the anchor. Approximately 5 lbs of tension will create an adequate knot.

Figure 13:
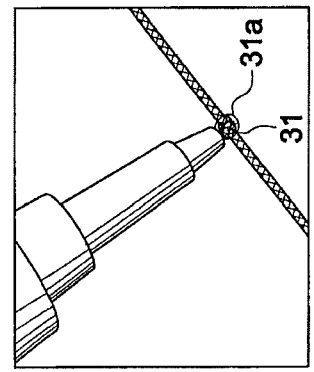

FIG. 13: Place a small amount of bonding agent 31*a* on the knot 31, favoring the short end of the knot. Cannot exist past about 0.5 mm from the long end of the knot. Allow adequate time to dry.

Figure 14:
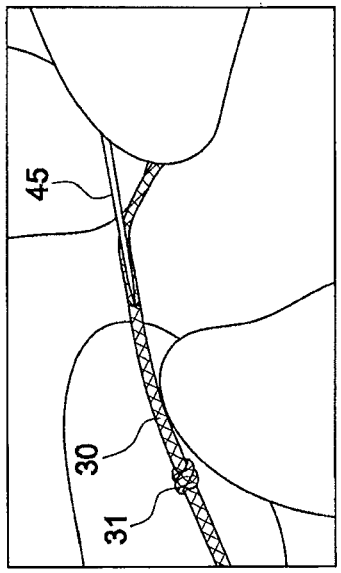

FIG. 14: Perform the next steps with a straight needle 45 with an attached nitinol loop 40. Any alternative suture passing device may be used as long as it allows the formation of the device 200 in FIG. 55. Pierce the braid 30 with the needle 45 about 10-20 mm from the long end of the knot 31.

Figure 15:
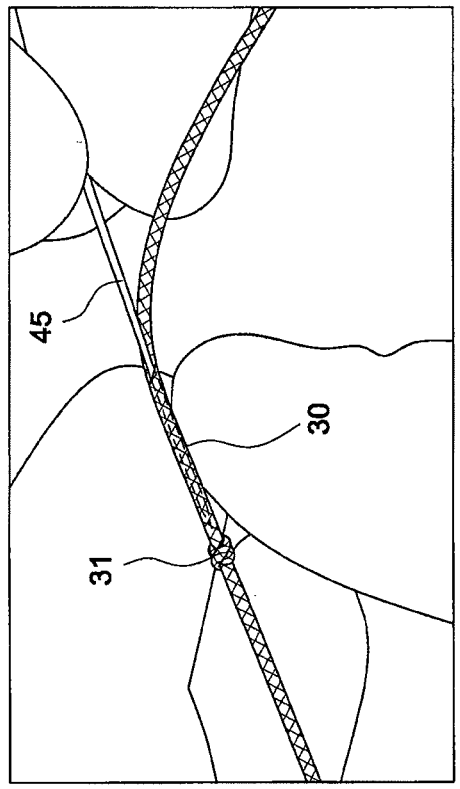

FIG. 15: Advance the needle 45 through the center of the braid 30, taking care not to penetrate the sheath with the tip of the needle.

Figure 16:
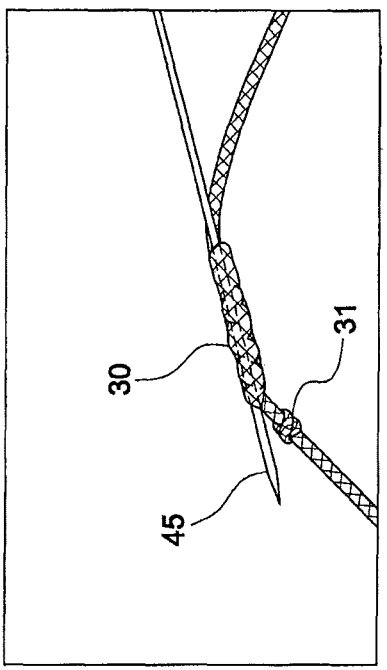

FIG. 16: Allow needle 45 to exit the sheath 30 between about 0.5 mm and 1 mm from the knot 31. The needle must not be passed through glued portions of the braid 30.

Figure 17:
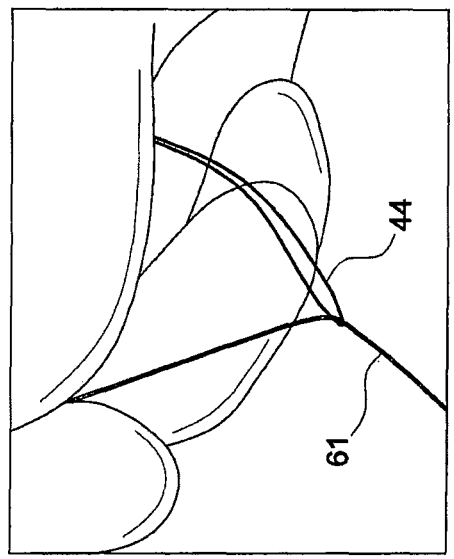

FIG. 17: Pass a small length of suture 61 (2-0 or smaller) through the open end 44 of the nitinol wire 40.

Figure 18:
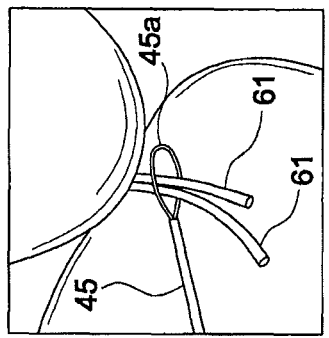

FIG. 18: Pass both free ends of the suture 61 through the loop on the needle 45 and fold the ends.

Figure 19:
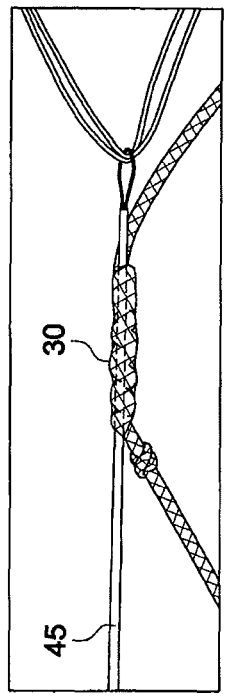

FIG. 19: Advance the needle 45 through the sheath 30 so the folded suture ends are passed through the center of the braid 30.

Figure 20:
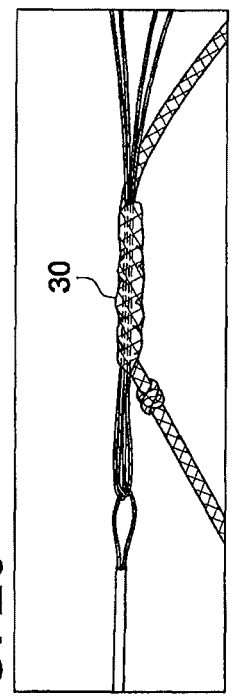

FIG. 20: Continue to pull the suture 61 through the braid 30 resulting in pulling the nitinol wire 40 through the center of the braid 30 as well.

Figure 21:
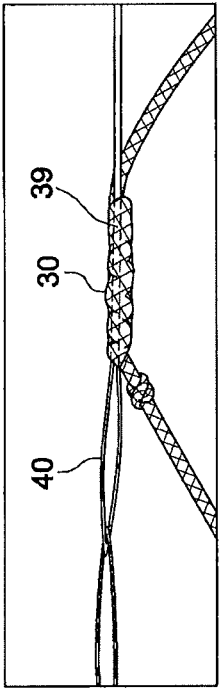

FIG. 21: Pull approximately half of the nitinol wire 40 through the braid splice 39. Ensure the shrink tube of the nitinol wire does not snag any portion of the splice 39.

Figure 22:
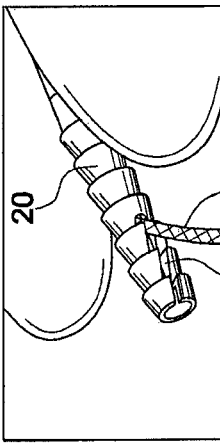

FIG. 22: Insert the long free end of the braid 30 into the side port of the anchor 20 that is on the same side as the cut slot (for example, cut slot 233).

Figure 23:
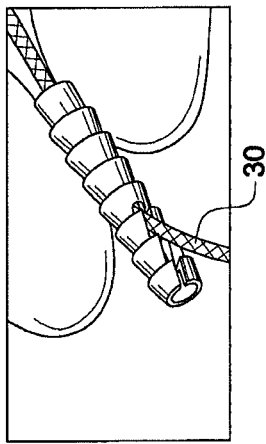

FIG. 23: Pull the braid 30 through the end hole.

Figure 24:
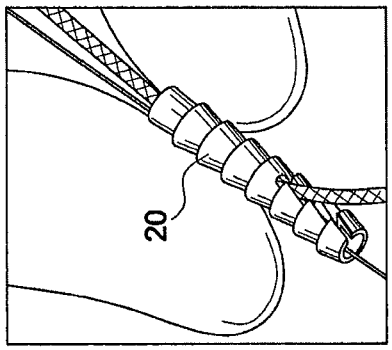

FIG. 24: Insert the non-looped end of the nitinol wire 40 through the same side port as the braid 30.

Figure 25:
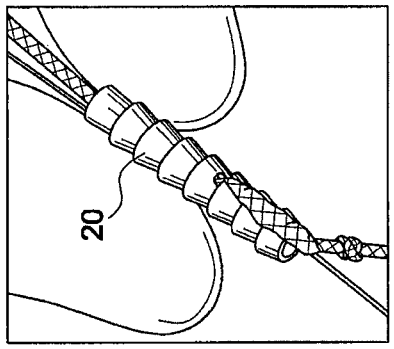

FIG. 25: Pull the nitinol 40 and the braid 30 evenly through the anchor 10 so the splice passes through the side port. Pass the splice 39 until there is sufficient access to the through hole across the side ports.

Figure 26:
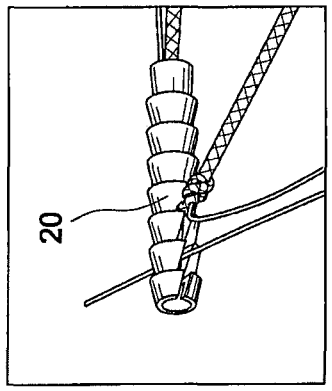

FIG. 26: Pass the looped end of the nitinol wire 40 through the side port access hole to the other side of the anchor. Pull until slack is removed.

Figure 27:
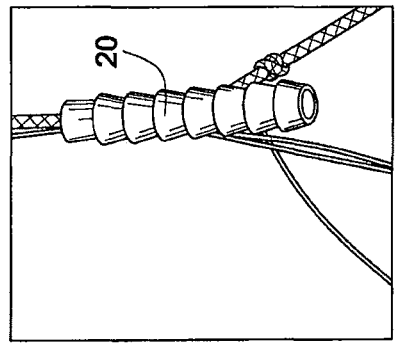

FIG. 27: Insert looped end of nitinol wire 40 back into side port and out the end hole.

Figure 28:
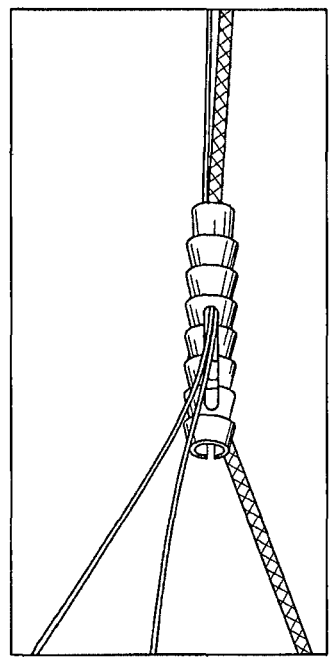

FIG. 28: Looped end of nitinol wire 40 should be on the opposite side of the post than the splice.

Figure 29:
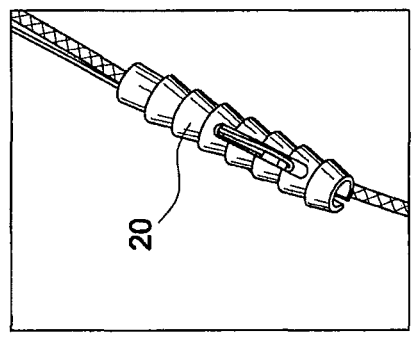

FIG. 29: Feed wire to remove all slack within and around the anchor.

Figure 30:
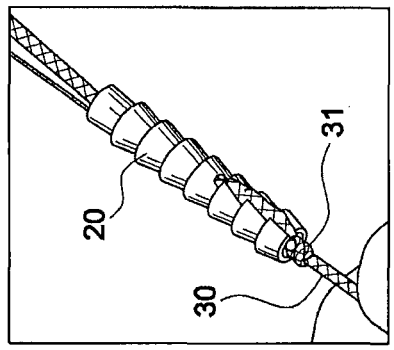

FIG. 30: Pull short end of braid 30 and knot 31 and relocate it through the cut slot 233 of the anchor.

Figure 31:
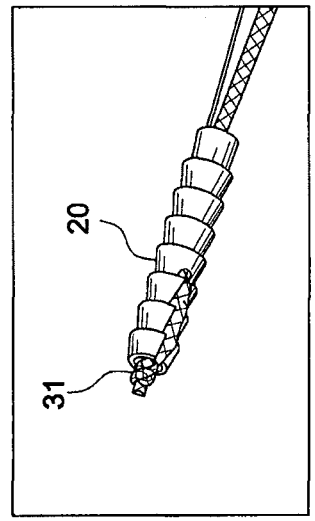

FIG. 31: Pull long end of braid 30 to seat knot 31 within the counterbore of the tip. Cut the remainder of the short end about 0.5-1.0 mm from the knot 31.

Figure 32:
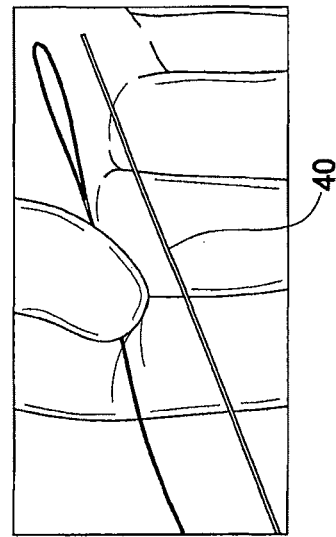

FIG. 32: Nitinol wire 40 should pull freely in both directions through the anchor 20 and braid splice 39. Adjust wire so both ends are even within about 0.5 inches.

Figure 33:
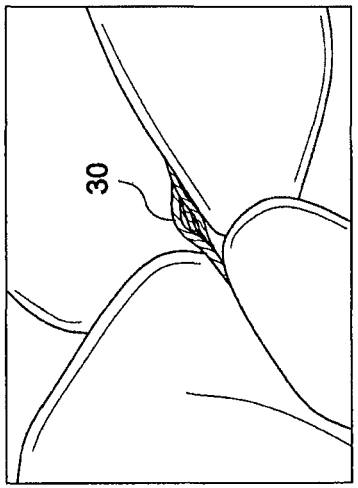

FIG. 33: From the end of the suture tail, measure about 11.0 inches to about 13.0 inches. At that point, pinch the suture and compress it as shown, to loosen the yarns within the braid.

Figure 34:
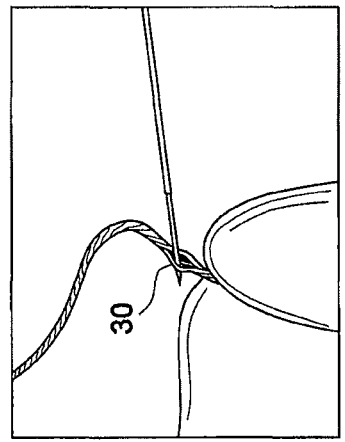

FIG. 34: With a needle, separate one of the yarns.

Figure 35:
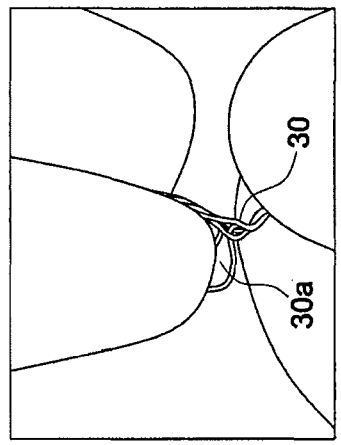

FIG. 35: Lightly pull some slack to form a small loop 30*a*.

Figure 36:
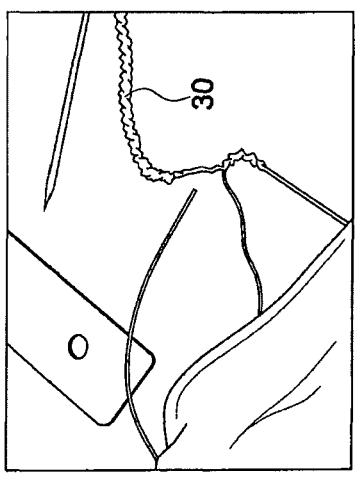

FIG. 36: Carefully pull the yarn from the direction of the free suture end out from the braided suture. The braid may wrinkle as a result. Limit the amount of wrinkling in the opposite direction of the free end by limiting pulling of the yarn from that direction.

Figure 37:
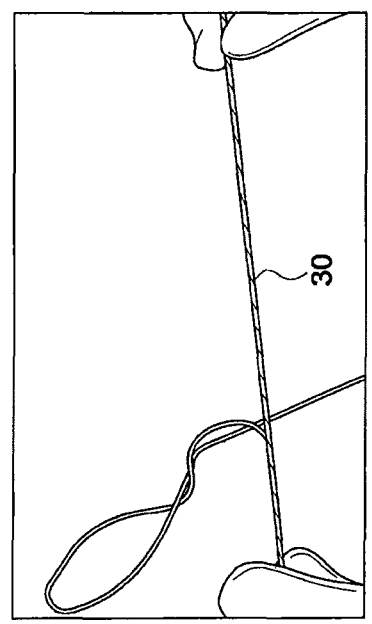

FIG. 37: Once the yarn is removed, the suture can be straightened out and smoothened, by pinching your finger and running it along the direction of the free end. This step is optional.

Figure 38:
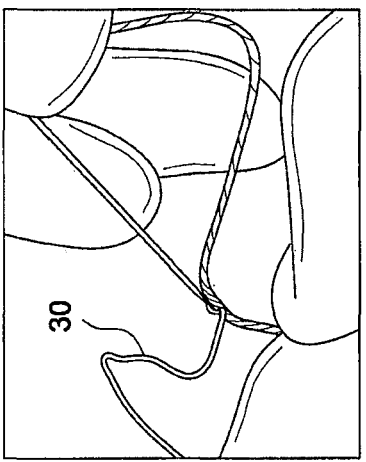

FIG. 38: Using the needle separate out a second non-white yarn from within about 0.5 inches of the site of the first yarn.

Figure 39:
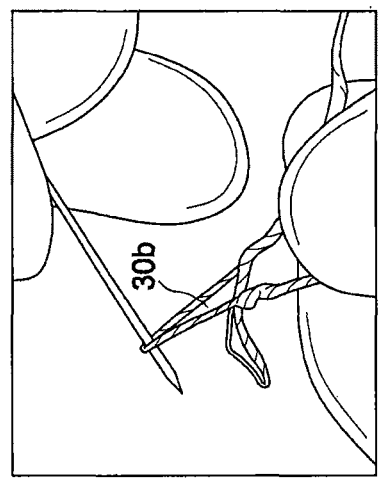

FIG. 39: Lightly pull some slack to form a small loop 30*b*.

Figure 40:
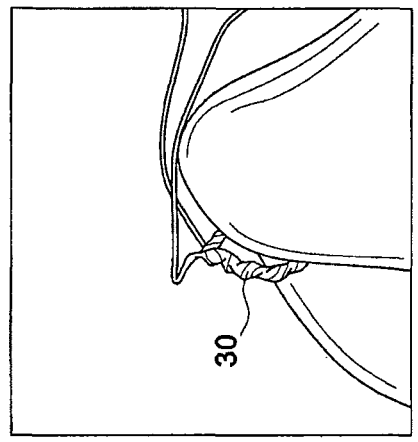

FIG. 40: Carefully pull the yarn from the direction of the free suture end out from the braided suture. The braid may wrinkle as a result. Limit the amount of wrinkling in the opposite direction of the free end, by limiting pulling of the yarn from that direction.

Figure 41:
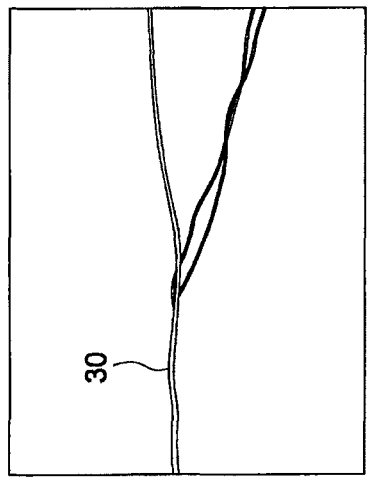

FIG. 41: Once the yarn is removed the suture can be straightened out and smoothened, by pinching your finger and running it along the direction of the free end. The result should be similar to the picture with two loose yarns branching off from the larger.

Figure 42:
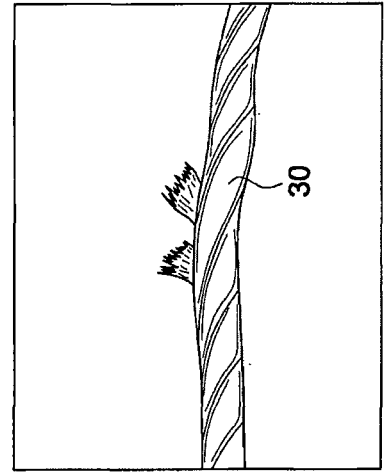

FIG. 42: The loose yarns shall be carefully trimmed close to the surface of the larger suture. The frayed edges should be pinched with the suture and brushed in the direction of the loose end, to limit how much it sticks out. Optional: step may be performed before smoothening the suture to facilitate blending the cut ends in.

Figure 43:
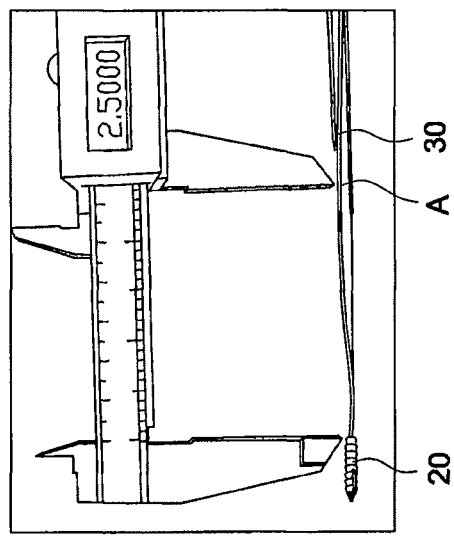

FIG. 43: Starting about 2.5 inches from the back edge of anchor 20, pierce the braid 30 and advance the needle through the center of the braid. This entry point A will further be called the entrance aperture.

Figure 44:
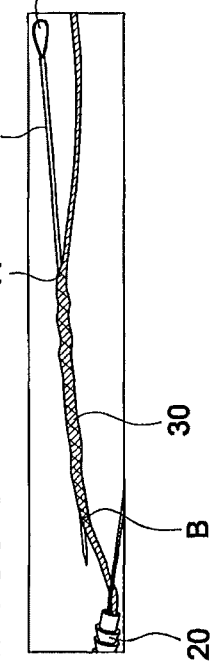

FIG. 44: As before, care must be taken not to penetrate the sheath 30 while advancing the needle 45.

Figure 45:
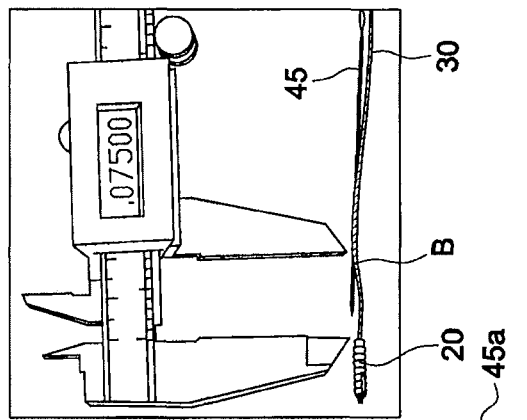

FIG. 45: Needle 45 should penetrate and create an exit aperture B at a maximum of about 0.75" from the end of anchor 20 but should not intersect the aperture created by nitinol wire 40.

Figure 46:
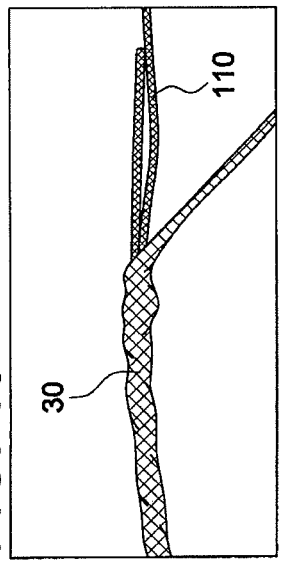

FIG. 46: Trim a sufficient length of a flexible strand 110 (for example, a suture 110 such as 2.0 FiberWire® suture 110) and pass it through the sheath using the needle. Pass it through until the end of strand 110 just enters the entrance aperture A and is fully contained. The excess suture at the exit aperture B should be trimmed as close to the braid of sheath 30 as possible.

Figure 47:
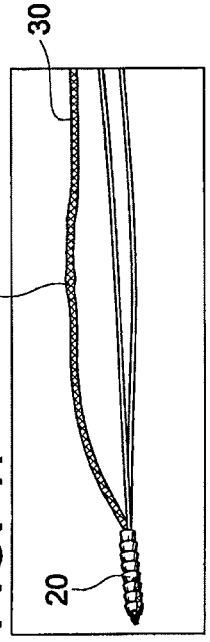

FIG. 47: To fully contain strand 110 within braid 30, pinch the entrance aperture A with one hand. With the other hand, take two fingers and pinch the sheath 30 and flatten it out in the direction of the exit aperture B. The sheath should envelop the remaining end of strand 110. Strand 110 should not protrude from the entrance aperture A. About 0.02" maximum protrusion is allowed from the entrance aperture A.

Figure 48:
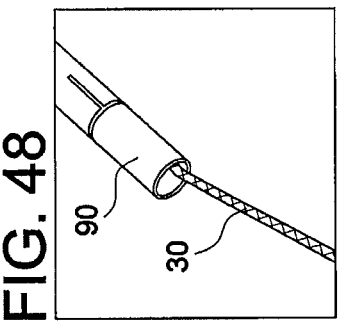

FIG. 48: Ensure there are no knots on the free end of the braid. Feed the free end of braid into the opening of driver 90, until it can be pulled from the opposite side.

Figure 49:
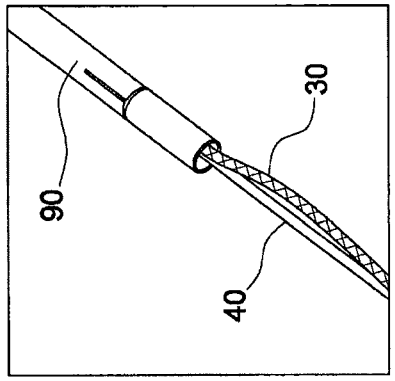

FIG. 49: Insert both ends of the nitinol wire 40 into the opening of the driver 90.

Figure 50:
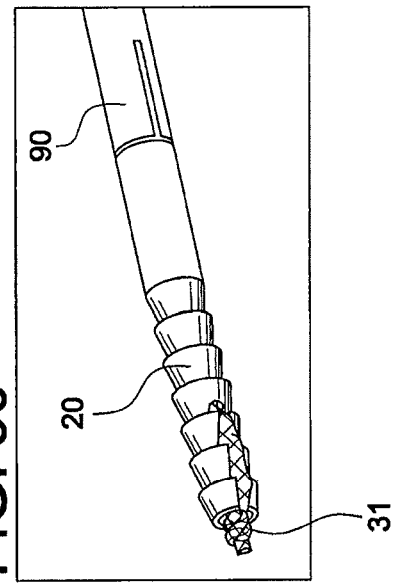

FIG. 50: Pull the slack of the braid 30 and the nitinol 40 so the anchor 20 seats in the counterbore of the driver 90.

Figure 51:
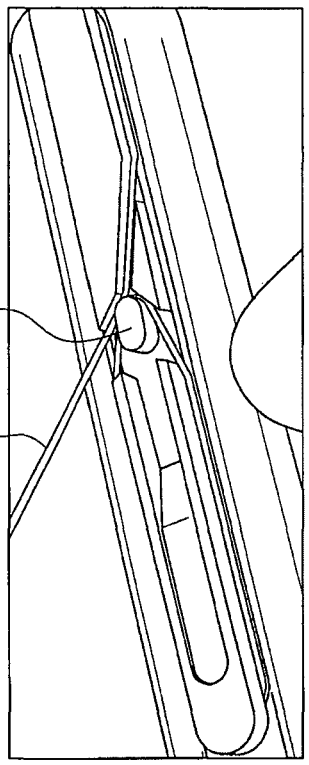

FIG. 51: Wrap the free end of the braid clockwise around keel 91 of the driver 90 once. Then pass it through the keel as shown.

Figure 52:
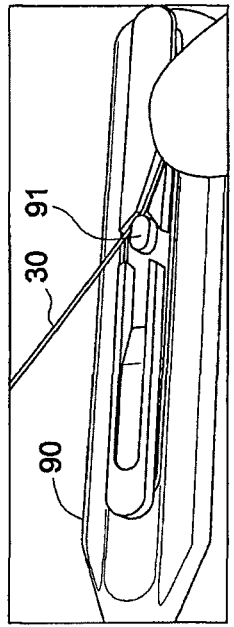

FIG. 52: Continue to pass the braid halfway around the keel counterclockwise.

Figure 53:
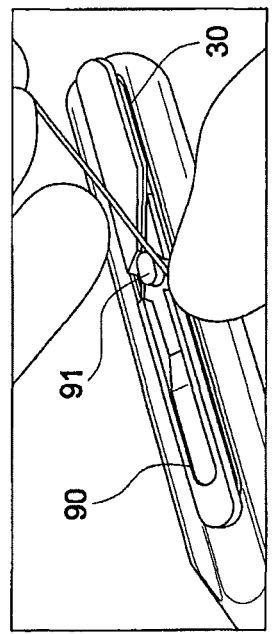

FIG. 53: Pass the braid back through the keel as shown.

FIG. 54: Result should look as shown. Approximately 0.5 to 1 inch of braid 30 should extend from keel. Trim excess braid (there should not be any tipped suture left on the end).

FIG. 55: Completed final assembly 200 formed of driver 90, suture anchor 20, nitinol wire 40, UHMWPE braid 30, and 2-0 FiberWire® suture 110.

Reference is now made to FIGS. 56-67 which illustrate detailed subsequent steps of methods of assembling exemplary surgical constructs of the present invention, i.e., surgical constructs comprising a tensionable knotless anchor (knotless SutureTak™) loaded with an insert in the form of a barbed suture (FIGS. 56-61) or in the form of a small cut-to-length piece of suture (FIGS. 62-67). Assembly instructions are provided below:

FIGS. 56-61: for inserting a piece of barbed suture 10 (cut from a barbed suture strand 10*a*) to form a surgical construct similar to surgical construct 100—the steps would happen between FIGS. 24 and 25 above but FIGS. 43-47 would be omitted.

Figure 56:
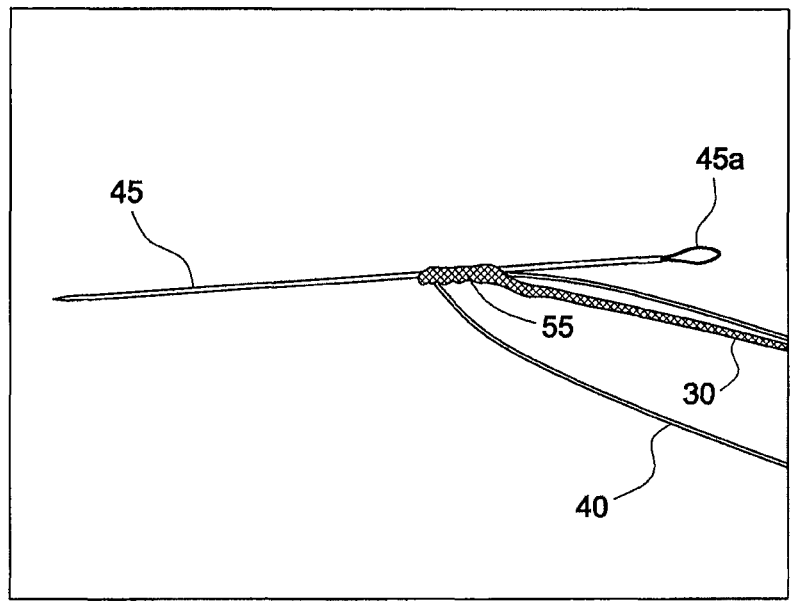
FIGS. 56-61 illustrate subsequent steps of a method of assembling a surgical construct of the present invention (with an insert in the form of an exemplary barbed suture).

FIG. 56: Insert needle 45 through splice 55 already made by the nitinol wire 40.

Figure 57:
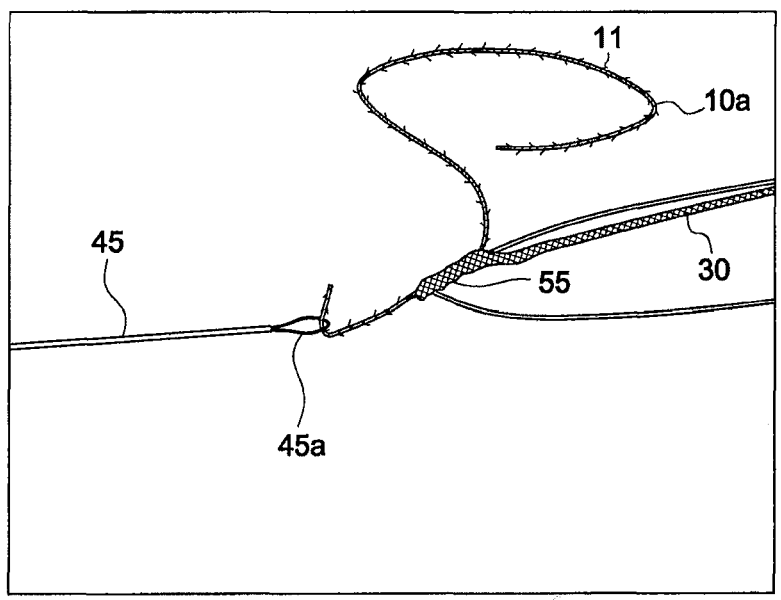

FIG. 57: Use eyelet 45*a* of needle 45 to shuttle barbed suture strand 10*a* with barbs 11 so that the direction of the barbs 11 allows passage through the splice 55.

Figure 58:
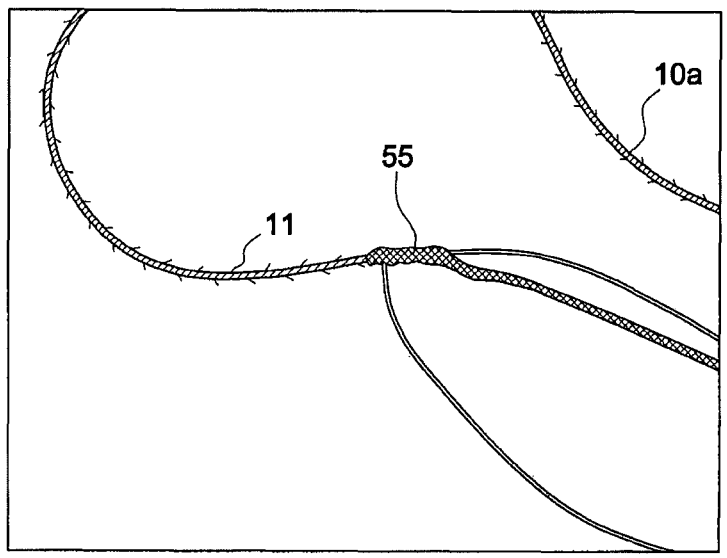

FIG. 58: Pull barbed suture 10*a* through the splice 55 until the suture end is barely protruding the splice 55.

Figure 59:
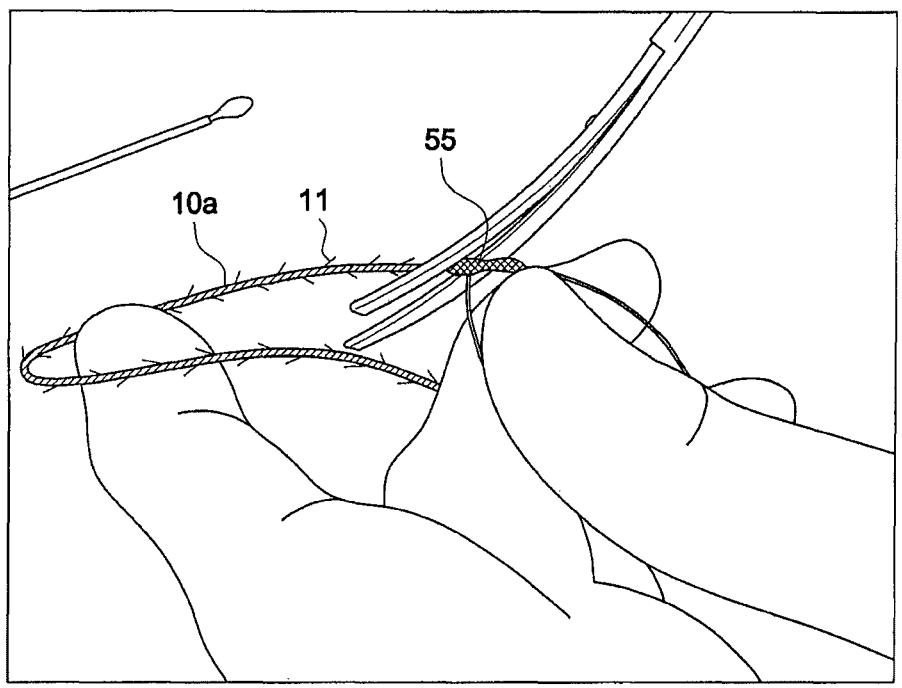

FIG. 59: Cut the excess suture 10*a*, flush with the splice 55, to obtain barbed suture 10 (with barbs 11).

Figure 60:
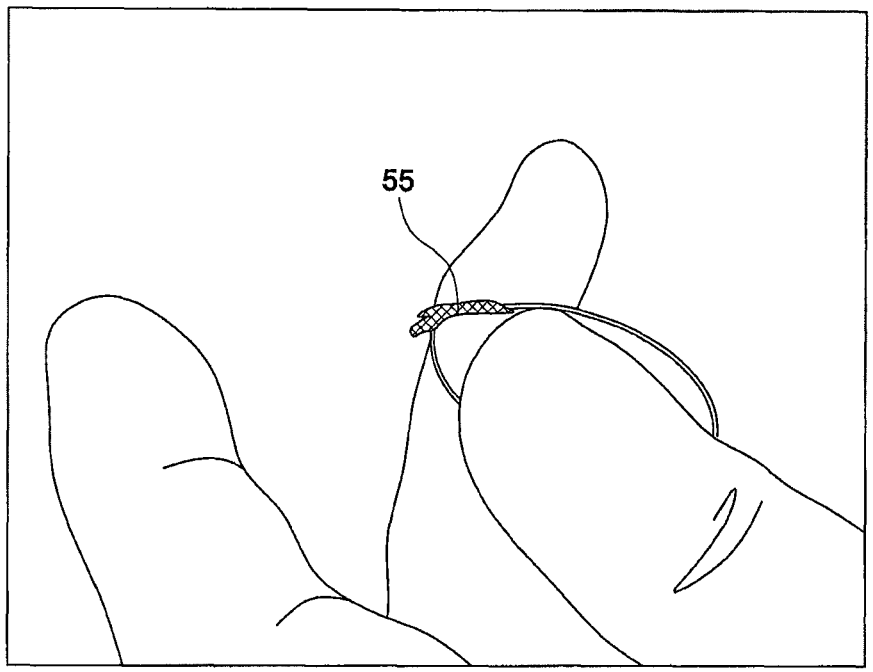

FIG. 60: Gently stretch the splice 55 so that the cut strand 10 is tucked inside the splice 55. A minor protrusion on the knotted side is allowed.

Figure 61:
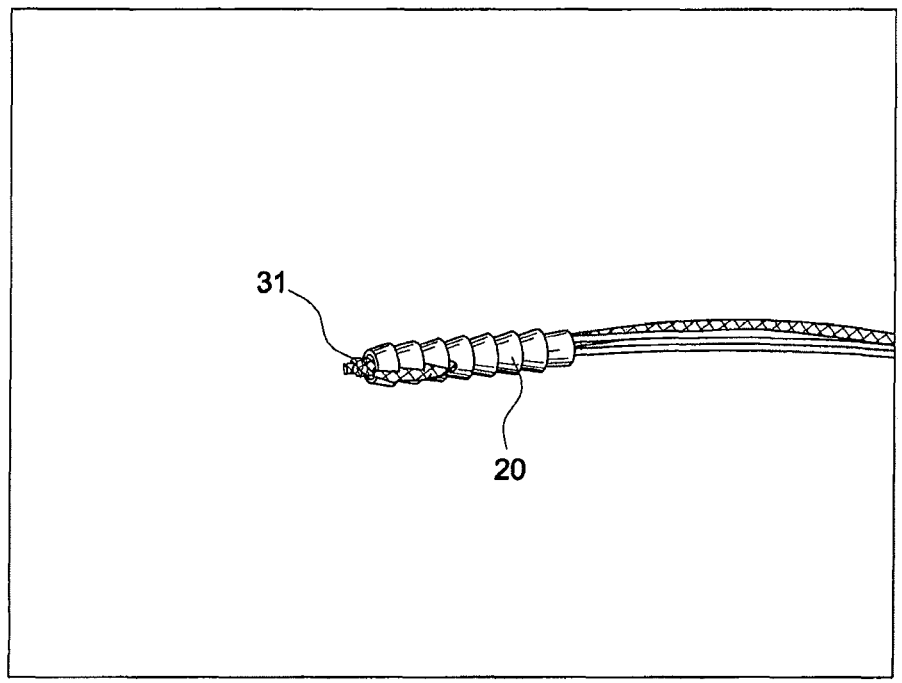

FIG. 61: Pull splice 55 and nitinol wire into the anchor 20 and position the knot 31 at the tip of the anchor 20.

FIGS. 62-67: for inserting a braid 110 (cut from a braid strand 110*a*) to form a construct similar to surgical construct 200—the steps would happen between FIGS. 24 and 25 above, but FIGS. 43-47 would be omitted.

Figure 62:
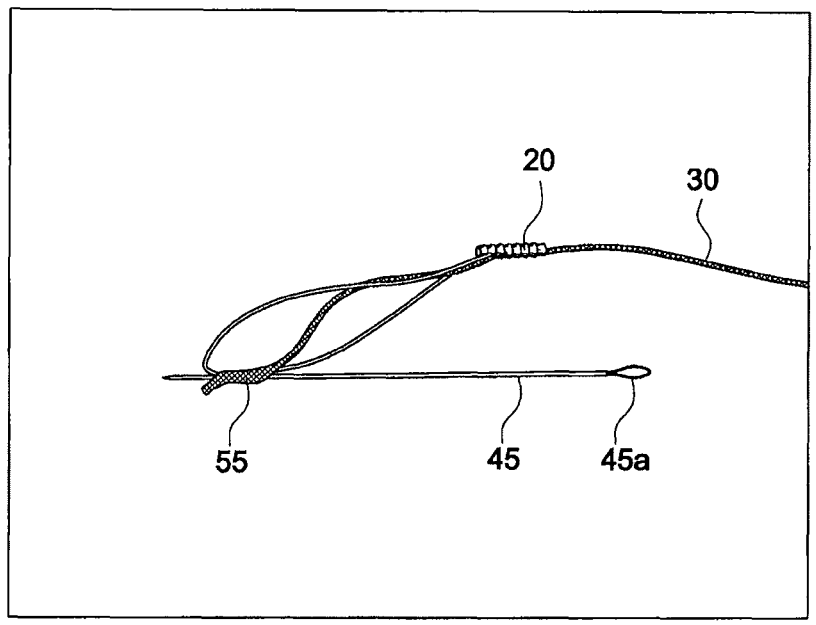
FIGS. 62-67 illustrate subsequent steps of a method of assembling a surgical construct of the present invention (with an insert in the form of an exemplary cut length of suture).

FIG. 62: Insert needle 45 through splice 55 already made by the nitinol wire.

Figure 63:
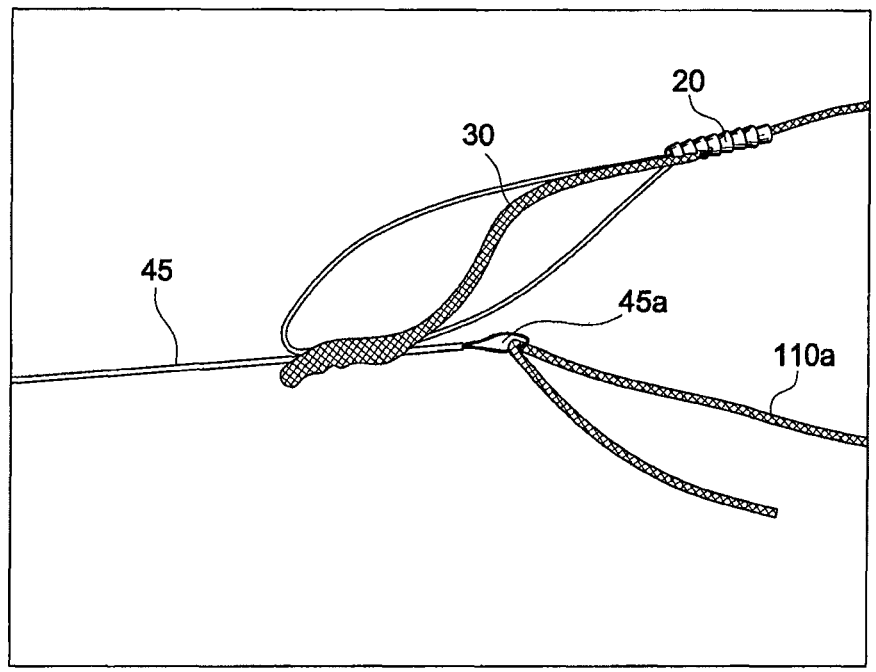

FIG. 63: Place cut length of suture 110*a* through the eyelet 45*a* of the needle 45 to shuttle it through the splice 55.

Figure 64:
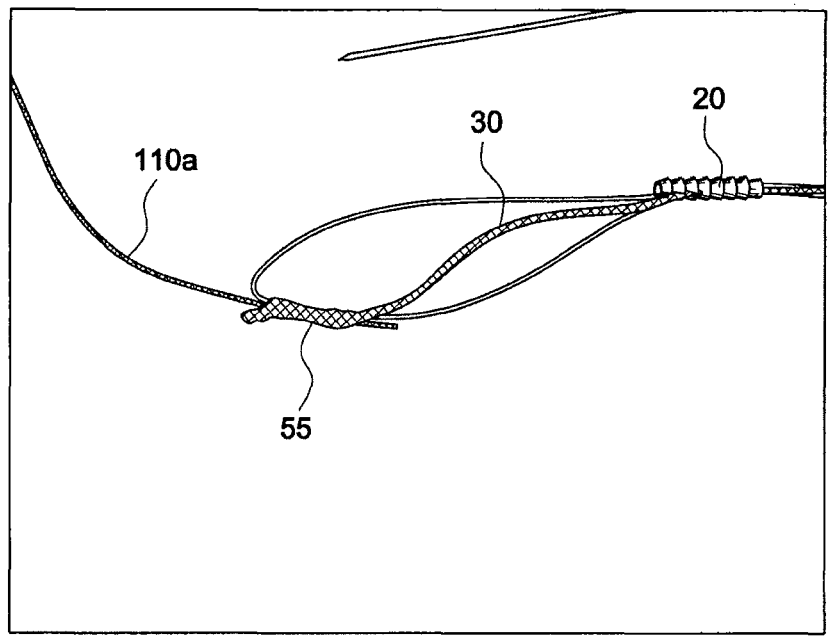

FIG. 64: Pull strand 110*a* through the splice 55 until the end of the strand 110*a* is barely protruding from the suture.

Figure 65:
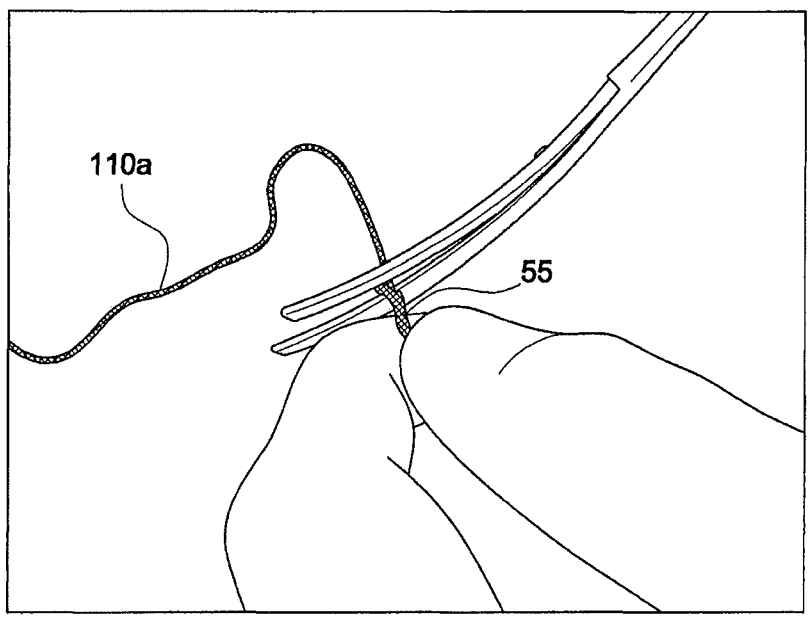

FIG. 65: Cut the excess suture 110a, flush with the splice 55, to obtain braid insert 110.

Figure 66:
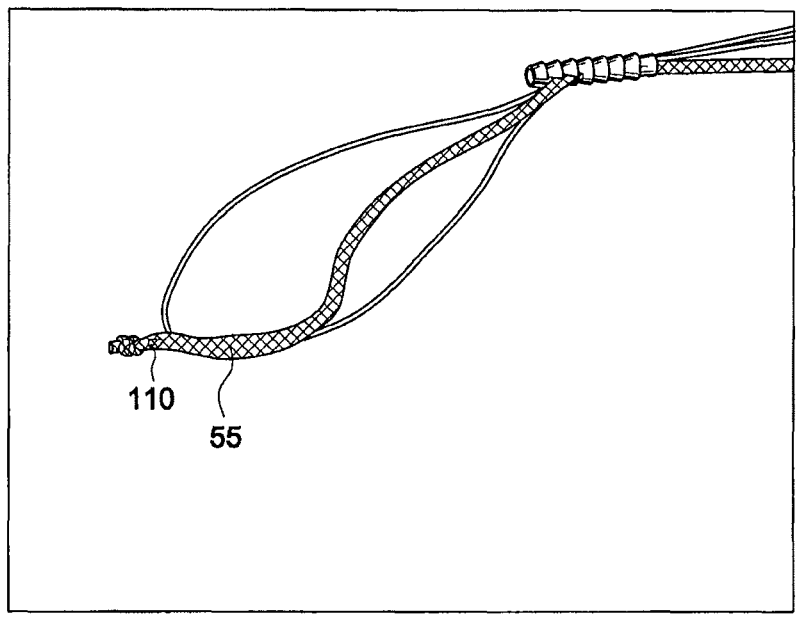

FIG. 66: Gently stretch the splice 55 so that the cut strand 110 is tucked inside the splice 55. A minor protrusion on the knotted side is allowed.

Figure 67:
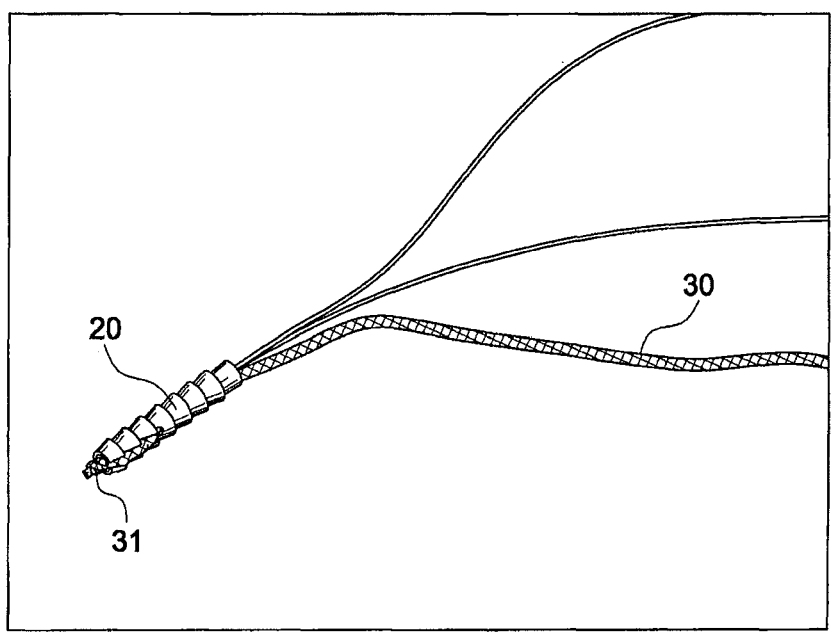

FIG. 67: Pull splice 55 and nitinol wire into the anchor 20 and position the knot 31 at the tip of the anchor 20.

In the embodiments where a fixation device (such as anchor 20) is employed (i.e., where the final surgical construct is not an "all suture" soft anchor), the anchor 20 may be a screw-in anchor or a push-in style anchor. Anchor 20 may be formed of metal, biocompatible plastic such as PEEK or a bioabsorbable PLLA material. Anchor 20 may be provided with a socket having any shape adapted to receive a driver tip for tapping or screw-in style anchors. Tensionable knotless anchor 20 may be made of one or more pieces, or may be provided as an integrated device.

The knotless suture constructs and systems of the present invention are used in conjunction with any knotless fixation devices which can allow a flexible strand and attached suture passing device and barbed insert to form a splice within the body of the fixation device. The fixation devices may be any of swivel and/or screw-in suture anchors and/or push-in suture anchors (such as an Arthrex SwiveLock® anchor, disclosed in U.S. Pat. No. 9,005,246 or a PushLock® anchor, as disclosed in U.S. Pat. No. 7,329,272). The fixation devices may be also any anchors, implants or screws (such as interference screws or tenodesis screws) or any fixation element that allows attachment/fixation of the knotless suture construct to bone. The fixation devices/implants may have various sizes (various diameters and/or lengths) and may be formed of biocompatible materials such as PEEK, biocomposite materials, metals and/or metal alloys, or combination of such materials, among others.

The flexible strand 30 may be a high-strength suture, such as an ultrahigh molecular weight polyethylene (UHMWPE) suture which is the preferred material as this material allows easy splicing. Alternatively, the high strength suture may be a FiberWire® suture, which is disclosed and claimed in U.S. Pat. No. 6,716,234, the entire disclosure of which is incorporated by reference in its entirety herein. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material.

The knotless suture constructs also include sutures that are spliced—at least in part—in a manner similar to an Arthrex ACL TightRope®, such as disclosed in U.S. Pat. Nos. 8,439,976 and 8,460,379, the disclosures of which are incorporated by reference in their entirety herein.

The systems and methods of the present invention have applicability to any tissue repair, for example, knotted or knotless tissue repairs such as attachment of soft tissue to bone, with particular applications to the tissue being tendon, labrum, Achilles tendon, rotator cuff, biceps or capsular tissue, among many others.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention.

What is claimed is:

1. A surgical system for tissue repairs, comprising:
a fixation device comprising a body, a longitudinal axis, a proximal end and a distal end; and
a tensionable construct pre-loaded on the fixation device, the tensionable construct including a flexible strand having a free end, and a splice, a locking insert that is a separate component from the flexible strand and is inserted into the splice, and a shuttling device threaded through the splice, the locking insert being configured to be moveable through the splice in a first direction with respect to the flexible strand and prevent movement through the splice with respect to the flexible strand in a second direction opposite the first direction.

2. The surgical system of claim 1, wherein the locking insert is a suture with a plurality of barbs or spikes.

3. The surgical system of claim 1, wherein the flexible strand is a coreless suture and the locking insert is a cut length of suture inserted along a center of the coreless suture to create a thicker portion.

4. The surgical system of claim 1, wherein the flexible strand is a suture formed of ultrahigh molecular weight polyethylene.

5. The surgical system of claim 1, wherein the shuttling device is a suture passing instrument.

6. The surgical system of claim 1, wherein the fixation device is an anchor.

7. The surgical system of claim 1, wherein the fixation device is an anchor with a post and a pair of openings symmetrically positioned relative to the post, the pair of openings extending in a direction about transversal to the longitudinal axis of the body, the pair of openings being configured to allow the tensionable construct to be passed through the body of the fixation device and around the post.

8. The surgical system of claim 1, wherein the shuttling device is configured to be pulled out of the body of the fixation device to allow the flexible strand to pass through the splice thereof within the body of the fixation device.

9. The surgical system of claim 1, wherein both the flexible strand and the shuttling device of the tensionable construct extend through the body of the fixation device, and wherein the shuttling device is configured to be pulled out of the body of the fixation device to allow the flexible strand to pass through an eyelet of the shuttling device and through the splice thereof to form a knotless closed loop.

10. The surgical system of claim 1, wherein the tissue is soft tissue.

11. The surgical system of claim 1, wherein the flexible strand has a fixed end opposite the free end.

\* \* \* \* \*